US00PP20079P2

(12) United States Plant Patent
van der Helm

(10) Patent No.: US PP20,079 P2
(45) Date of Patent: Jun. 9, 2009

(54) CARNATION PLANT NAMED 'ALLURA'

(50) Latin Name: *Dianthus caryophyllus*
Varietal Denomination: Allura

(75) Inventor: Franciscus Jacobus Joseph van der Helm, Aalsmeer (NL)

(73) Assignee: P. Kooij & Zonen B.V., Aalsmeer (NL)

( * ) Notice: Subject to any disclaimer, the term of this patent is extended or adjusted under 35 U.S.C. 154(b) by 0 days.

(21) Appl. No.: 12/154,246

(22) Filed: May 21, 2008

(51) Int. Cl.
*A01H 5/00* (2006.01)

(52) U.S. Cl. ..... Plt./272

(58) Field of Classification Search ..... Plt./272
See application file for complete search history.

*Primary Examiner*—Annette H Para
(74) *Attorney, Agent, or Firm*—C. A. Whealy

(57) ABSTRACT

A new and distinct cultivar of Carnation plant named 'Allura', characterized by its compact, upright, somewhat outwardly spreading and mounded plant habit; moderately vigorous growth habit; freely branching habit; freely flowering habit; large double red purple-colored flowers that are positioned above and beyond the foliage; and good flower longevity.

1 Drawing Sheet

Botanical designation: *Dianthus caryophyllus.*
Cultivar denomination: 'ALLURA'.

BACKGROUND OF THE INVENTION

The present invention relates to a new and distinct cultivar of Carnation plant, botanically known as *Dianthus caryophyllus,* grown as a potted plant, and hereinafter referred to by the name 'Allura'.

The new Carnation is a product of a planned breeding program conducted by the Inventor in Aalsmeer, The Netherlands. The objective of the breeding program was to develop new freely-branching Carnation cultivars with numerous flowers and attractive flower coloration.

The new Carnation originated from a cross-pollination made by the Inventor during the summer of 2004, of a proprietary selection of *Dianthus caryophyllus* identified as code number A16165-01, not patented, as the female, or seed, parent with a proprietary selection of *Dianthus caryophyllus* identified as code number A06259-03, not patented, as the male, or pollen, parent. The cultivar Allura was discovered and selected by the Inventor as a flowering plant within the progeny of the stated cross-pollination in a controlled greenhouse environment in Aalsmeer, The Netherlands during the spring of 2005.

Asexual reproduction of the new cultivar by terminal cuttings propagated in a controlled greenhouse environment in Aalsmeer, The Netherlands since the spring of 2005, has shown that the unique features of this new Carnation are stable and reproduced true to type in successive generations of asexual reproduction.

SUMMARY OF THE INVENTION

The new Carnation has not been observed under all possible environmental conditions. The phenotype may vary somewhat with variations in environment such as temperature and light intensity, without, however, any variance in genotype.

The following traits have been repeatedly observed and are determined to be the unique characteristics of 'Allura'. These characteristics in combination distinguish 'Allura' as a new and distinct cultivar of Carnation:

1. Compact, upright, somewhat outwardly spreading and mounded plant habit.
2. Moderately vigorous growth habit.
3. Freely branching habit.
4. Freely flowering habit.
5. Large double red purple-colored flowers that are positioned above and beyond the foliage.
6. Good flower longevity.

Plants of the new Carnation differ from plants of the female parent selection in the following characteristics:

1. Plants of the new Carnation are more uniform in plant shape than plants of the female parent selection.
2. Plants of the new Carnation have larger flowers than plants of the female parent selection.

Plants of the new Carnation differ from plants of the male parent selection primarily in growth habit as plants of the new Carnation are more compact than plants of the male parent selection.

Plants of the new Carnation can be compared to plants of the Carnation 'Pink Surprise', not patented. In side-by-side comparisons conducted in Aalsmeer, The Netherlands, plants of the new Carnation differed from plants of 'Pink Surprise' in the following characteristics:

1. Plants of the new Carnation were larger than plants of 'Pink Surprise'.
2. Plants of the new Carnation were more freely flowering than plants of 'Pink Surprise'.
3. Plants of the new Carnation had larger flowers than plants of 'Pink Surprise'.
4. Flower color of plants of the new Carnation was more stable than flower color of plants of 'Pink Surprise'.

BRIEF DESCRIPTION OF THE PHOTOGRAPH

The accompanying photograph illustrates the overall appearance of the new Carnation. This photograph shows the colors as true as it is reasonably possible to obtain in colored reproductions of this type. Colors in the photograph may differ slightly from the color values cited in the detailed botanical description which accurately describe the colors of the new Carnation. The photograph comprises a side perspective view of a typical flowering plant of 'Allura' grown in a container.

DETAILED BOTANICAL DESCRIPTION

In the following description, color references are made to The Royal Horticultural Society Colour Chart, 1995 Edition, except where general terms of ordinary dictionary significance are used. Measurements and numerical values represent averages for typical flowering plants. The aforementioned photograph and following observations and measurements describe plants grown in Aalsmeer, The Netherlands during the summer in a glass-covered greenhouse and under conditions and practices which approximate those generally used in commercial potted Carnation production. During the production of the plants, day temperatures averaged 20° C., night temperatures averaged 14° C. and light levels averaged 7,000 lux. Single plants were grown in 10-cm pots and were pinched one time. Plants were five months old when the photograph and the detailed description were taken.

Botanical classification: *Dianthus caryophyllus* 'Allura'.

Parentage:

*Female, or seed, parent.*—Proprietary selection of *Dianthus caryophyllus* identified as code number A16165-01, not patented.

*Male, or pollen, parent.*—Proprietary selection of *Dianthus caryophyllus* identified as code number A06259-03, not patented.

Propagation:

*Type.*—Terminal cuttings.

*Time to initiate roots, summer.*—About seven days at 25° C.

*Time to initiate roots, winter.*—About ten days at 20° C.

*Time to produce a rooted young plant, summer.*—About 20 days at 25° C.

*Time to produce a rooted young plant, winter.*—About 30 days at 20° C.

*Root description.*—Fine; white in color.

*Rooting habit.*—Freely branching.

Plant description:

*Plant form.*—Compact, upright, somewhat outwardly spreading and mounded plant habit; inverted triangle.

*Growth and branching habit.*—Moderately vigorous and freely-branching growth habit; when pinched, lateral branches potentially forming at every node; dense and bushy growth habit.

*Plant height.*—About 16 cm.

*Plant diameter or spread.*—About 17 cm.

*Lateral branches.*—Length: About 9.8 cm. Diameter: About 3 mm. Internode length: About 2.4 cm. Texture: Smooth, glabrous; waxy. Color: Close to 191A.

*Foliage description.*—Arrangement: Opposite, simple; sessile. Length: About 8.2 cm. Width: About 1.1 cm. Shape: Lanceolate. Apex: Acute. Base: Truncate. Margin: Entire. Texture, upper and lower surfaces: Smooth, glabrous; waxy. Venation pattern: Pinnate. Color: Developing foliage, upper and lower surfaces: Close to 137D. Fully expanded foliage, upper and lower surfaces: Close to 189A; venation, close to 189A.

*Flower description.*—Flower type and habit: Large double flowers. Freely flowering habit; usually 65 flowers developing per plant. Flowers positioned above and beyond the foliage; flowers facing upright and outwardly. Flowers faintly fragrant; clove-like. Natural flowering season: Flowering is continuous through the summer in The Netherlands. Plants begin flowering about three months after planting. Flowers last about ten days on the plant. Flowers persistent. Flower diameter: About 4.8 cm. Flower depth: About 4.4 cm. Flower buds: Length: About 2.4 cm. Diameter: About 1.1 cm. Shape: Elliptical. Color: Close to 137C. Petals/petaloids: Quantity/arrangement: About 38 per flower in several whorls. Length, outer petals: About 4.6 cm. Width, outer petals: About 2.6 cm. Shape: Roughly spatulate. Apex: Emarginate. Base: Acute. Margin: Entire. Texture, upper and lower surfaces: Smooth, glabrous. Color: When opening and fully opened, upper surface: Close to 67B. When opening and fully opened, lower surface: Close to 67B. Sepals: Quantity/arrangement: Five fused in a single whorl. Length: About 2.8 cm. Width: About 8 mm. Shape: Lanceolate. Apex: Acuminate. Margin: Entire. Texture, upper and lower surfaces: Smooth, glabrous; waxy. Color, upper surface: Close to 137C. Color, lower surface: Close to 157D. Peduncles: Length: About 8 mm. Diameter: About 2 mm. Strength: Moderately strong. Texture: Smooth, glabrous. Color: Close to 137C.

*Reproductive organs.*—Stamens: Quantity: About 14 per flower. Anther length: About 3 mm. Anther shape: Oblong. Anther color: Close to 36B. Pollen amount: Moderate. Pollen color: Close to 10B. Pistils: Quantity: About two per flower. Pistil length: About 3.2 cm. Stigma shape: Curled. Stigma color: Close to 36D. Style length: About 2.9 cm. Style color: Close to 68D. Ovary color: Close to 145B.

*Seeds.*—Quantity: Five per capsule. Length: About 4 mm. Diameter: About 3 mm. Color: Close to 202A.

Disease/pest resistance: Plants of the new Carnation have not been observed to be resistant to pathogens and pests common to Impatiens.

Temperature tolerance: Plants of the new Carnation have been observed to tolerate temperatures ranging from about −2° C. to 35° C.

It is claimed:

1. A new and distinct Carnation plant named 'Allura' as illustrated and described.

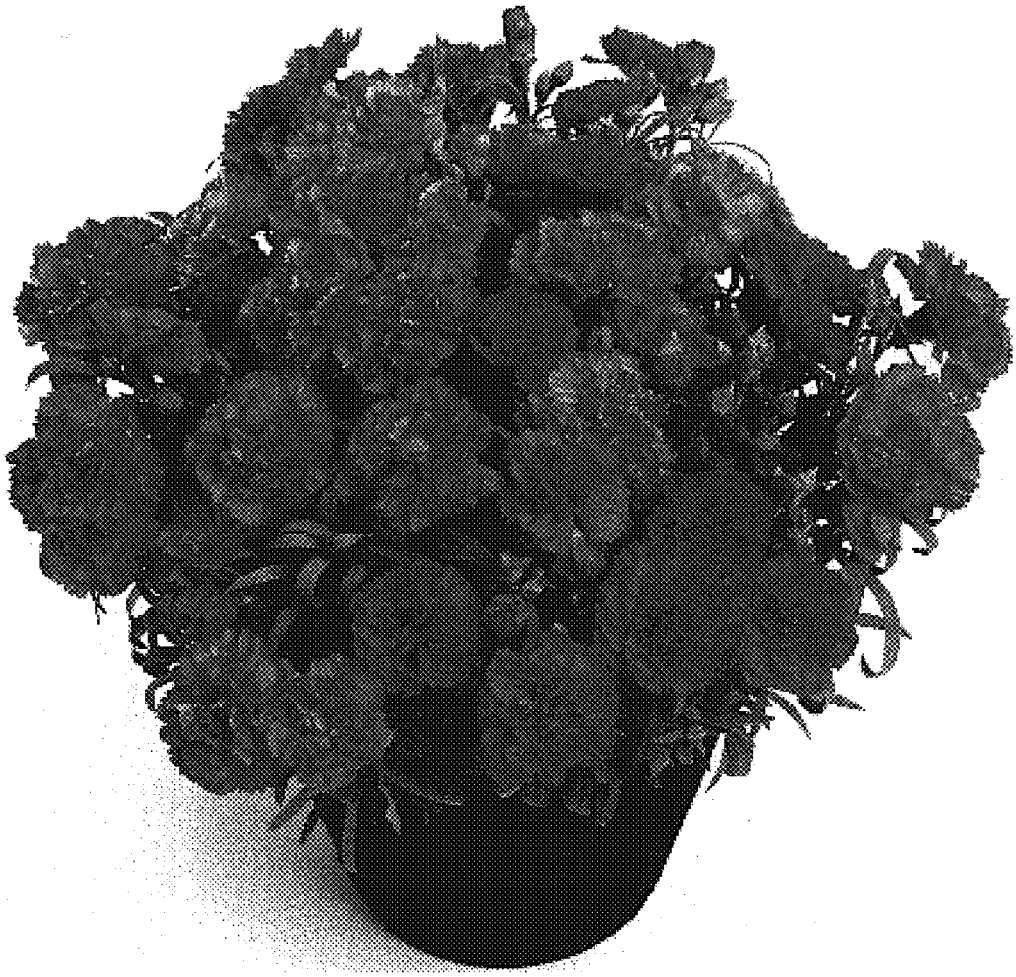

* * * * *